United States Patent [19]

Kaufman

[11] Patent Number: 5,014,723

[45] Date of Patent: * May 14, 1991

[54] ARTICLES FOR PROTECTION OF LIVING TISSUES

[76] Inventor: Jack W. Kaufman, 357 Frankel Blvd., Merrick, N.Y. 11556

[*] Notice: The portion of the term of this patent subsequent to Jul. 22, 2003 has been disclaimed.

[21] Appl. No.: 355,086

[22] Filed: May 18, 1989

Related U.S. Application Data

[63] Continuation of Ser. No. 91,655, Sep. 1, 1987, abandoned, which is a continuation-in-part of Ser. No. 887,262, Jul. 21, 1986, abandoned, which is a continuation-in-part of Ser. No. 852,797, Apr. 16, 1986, abandoned, which is a continuation-in-part of Ser. No. 602,602, Apr. 20, 1984, Pat. No. 4,601,286.

[51] Int. Cl.$^5$ .............................................. A61B 19/08
[52] U.S. Cl. ...................... 128/853; 128/82.1; 128/849; 604/368
[58] Field of Search .................. 128/155, 156, 82.1, 128/849, 850, 853, 856, 207.14, 207.15, 3, 4, 303.1; 604/265, 266, 368

[56] References Cited

U.S. PATENT DOCUMENTS

| | | | |
|---|---|---|---|
| 3,862,452 | 1/1975 | Wichterle et al. | 128/334 R X |
| 3,901,236 | 8/1975 | Assarsson et al. | 604/368 |
| 3,975,350 | 8/1976 | Hudgin et al. | 128/127 X |
| 4,053,442 | 10/1977 | Jungr et al. | 264/2.2 X |
| 4,058,124 | 11/1977 | Yen et al. | 604/376 X |
| 4,085,168 | 4/1978 | Milkovich et al. | 524/910 X |
| 4,173,606 | 11/1979 | Stoy et al. | 623/2 X |
| 4,362,841 | 12/1982 | Minatono et al. | 128/156 X |
| 4,390,656 | 6/1983 | Weise et al. | 524/493 |
| 4,411,885 | 10/1983 | Barels et al. | 424/49 X |
| 4,452,776 | 6/1984 | Refojo | 264/25 X |
| 4,468,229 | 8/1984 | Su | 8/543 X |
| 4,489,722 | 12/1984 | Ferraro et al. | 128/207.15 |
| 4,524,064 | 6/1985 | Nambu | 514/944 X |
| 4,548,979 | 10/1985 | Weise et al. | 524/403 |
| 4,601,286 | 7/1986 | Kaufman | 128/132 D |
| 4,710,194 | 12/1987 | Kelman | 623/6 |

*Primary Examiner*—Robert A. Hafer
*Assistant Examiner*—Kevin G. Rooney
*Attorney, Agent, or Firm*—Seymour G. Bekelnitzky

[57] ABSTRACT

An article useful in laser-effected surgery and therapy on humans and animals which reduces or eliminates undesired exposure of said humans, animals and other articles to said lasers comprising
(a) a first member proximal to the laser source comprising a xerogel comprising at least one hydrophilic water-insoluble polymer;
(b) a second, backing member;
(c) water;

wherein, if desired, said xeogel layer further comprises at least one additive selected from the group consisting of pharmaceutically acceptable salts, colorants, including pigments, and medications.

The invention further comprises an article comprising at least one metallic layer disposed between said xerogel and backing members the proximal surface of said metallic layer being reflective or non-reflective of the laser beams as required.

If desired adhesives may also be disposed between the layers of the article and/or between the article and the surface to be protected.

32 Claims, 3 Drawing Sheets

FIG.5
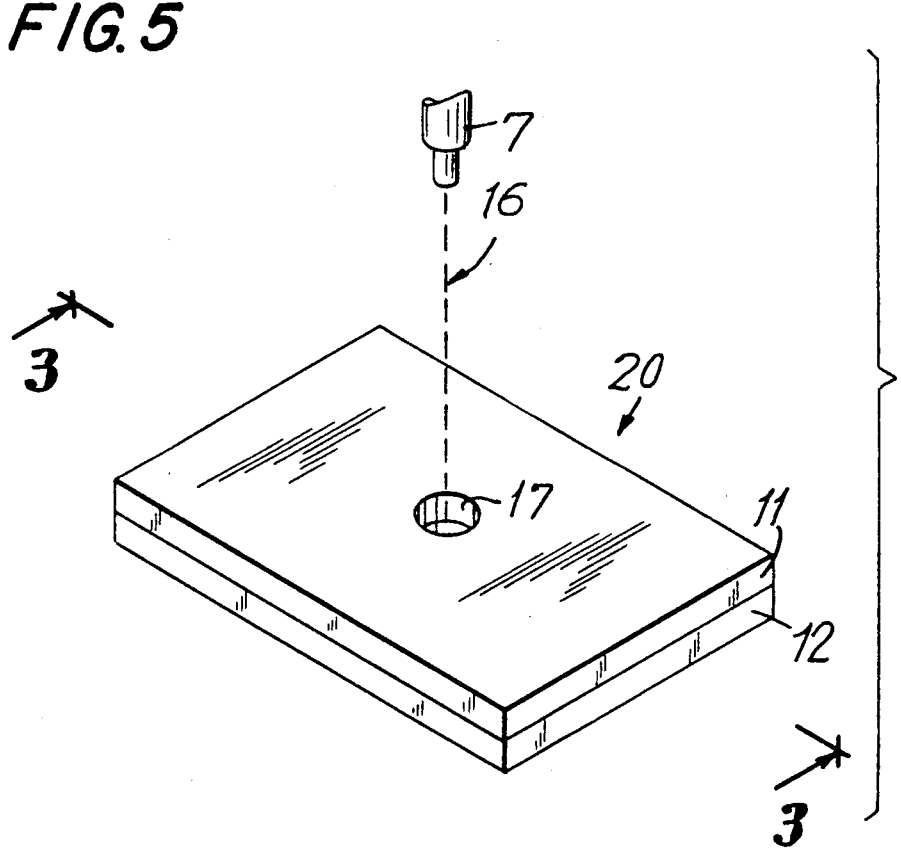
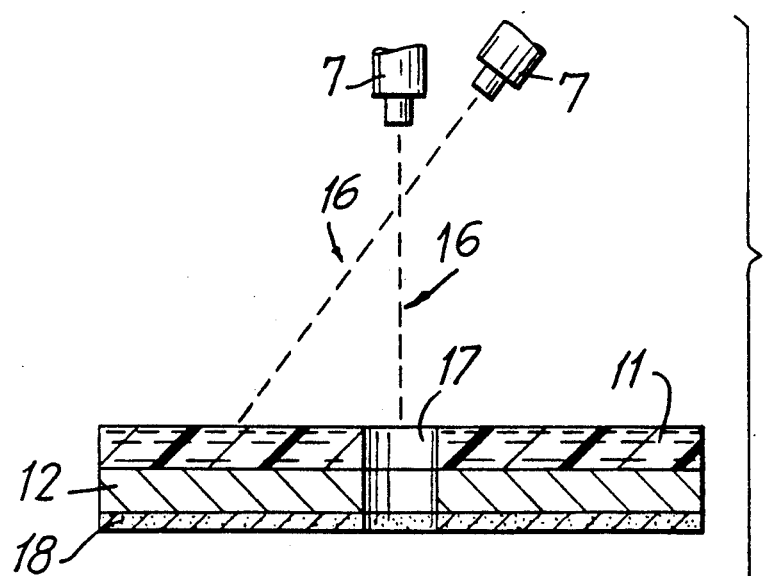
FIG.6

ARTICLES FOR PROTECTION OF LIVING TISSUES

This is a continuation of application Ser. No. 091,655, filed 9/01/87 now abandoned, which is a continuation-in-part of my copending application Ser. No. 887,262 filed Jul. 21, 1986 now abandoned, which was a continuation-in-part of my copending application Ser. No. 852,797 filed Apr. 16, 1986, now abandoned, which was a continuation-in-part of my copending application Ser. No. 602,602 filed Apr. 20, 1984 now U.S. Pat. No. 4,601,286 issued Jul. 22, 1986.

BACKGROUND OF THE INVENTION

This invention relates to articles for the prevention of undesired exposure of humans, animals and articles to laser beams. More particularly, it relates to protective barriers such as protective clothing, sheaths for instruments, surgical drapes, endotracheal tubes, vaginal dilators and the like, for use in or during laser-effected surgery or therapy which are useful in the protection of such humans, animals and articles from said undesired exposure to said lasers, said barriers being comprised of hydrophilic xerogels or hydrogels and, if desired, additional additives such as salts, colorants, pigments and medications.

Lasers have recently made a significant breakthrough as a preferred, in some, and the *only* modality, in other surgical and therapeutic areas. These areas of increasing use of lasers in surgery and other treatments include, e.g., otolaryngology, gynecology and ophthalmology.

Amongst the main advantages of lasers, in surgery, are their ability to incise and/or remove precisely controlled areas of tissue while permitting visual assessment of the procedure through use of an operating microscope. This visual assessment is facilitated by reduction of bleeding and absence of other instrumentation, which might block the surgeon's view, in laser surgery when compared to conventional surgical techniques.

Furthermore, if the blood vessels are sufficiently small they are sealed, by the laser, after incision. If some bleeding were to occur, for instance, in the case of larger blood vessels it can be efficiently stopped by coagulation using a defocused beam, the defocusing being accomplished by partial retraction of the focusing tip, i.e., by increasing the working distance of the laser beam.

Additional advantages of using lasers in surgery are the limitation of the area of undesirable tissue destruction and the zone of devitalized tissue, fewer post-operative complications and less post-operative pain and scar formation which might hinder healing. As a consequence hospitalization time is reduced.

Nevertheless, the use of lasers, in medical treatments and surgery, is not without disadvantages and hazards, chief among which are the danger of fire and the destruction of viable tissue on the margins, or periphery, of the operative site.

As a consequence normal drape procedures commonly used in laser surgery and treatment are of limited value and potentially dangerous. For instance, a fire hazard is especially present when wet Cottonoids (cotton gauze pads wet with saline) which are used to protect the surrounding tissues and organs from exposure to extraneous laser beams, whether direct or reflected, dry out and ignite due to the high inflammability of dry cotton or cellulosics. This is an always present danger due to the high levels of energy associated with laser beams. Thus, it is necessary for the surgical team to be constantly aware of that possibility and to keep the gauze moistened at all times.

Yet other problems arise in the use of drapes on compound surfaces, i.e. surfaces that are not smooth but rather have cavities and ridges, whereby the usual drapes do not conform to the surface topography thereby permitting gaps to be formed between the tissue surface and drape. These gaps permit the gathering of gases and/or heat therein which ultimately result in undesirable tissue damage.

Furthermore, stray beams may impinge on personnel and articles within the operating arena with concomitant damage thereto, e.g., burning the skin of said personnel, charring of clothing, melting of plastic articles, ignition of flammable materials, overheating of equipment, and the like. A. H. Andrews, Jr., and Polanyi, T. G., "Hazards and Safety Considerations When Using the $CO_2$ Laser" in A. G. Andrews, Jr. (ed.): *Microscopic and Endoscopic Surgery With the $CO_2$Laser*, Boston, MA., John Wright-PSG, Inc., pp75-6, 1982.

An additional aspect of the fire hazard is that the laser beam will burn through most plastics or rubbers of which tubes for insertion into body cavities, e.g., endotracheal tubes and vaginal drapes or dilators, are constructed. Thus, the use of plastic or most rubber endotracheal tubes is usually contraindicated when surgery employing lasers is contemplated. Therefore red rubber tubing or steel, which are less sensitive to lasers, are used, e.g., in the construction of endotracheal tubes. However, because endotracheal tubes prepared from such materials lack built-in cuffs, they do not make completely air-tight seals with the organ walls. To get around that problem it has been necessary to place a separable, inflatable cuff over the distal end of the tube which has, therefore, resulted in the addition of a balloon-filling tube, passed through the larynx, to an already crowded lumen. Furthermore, if the beam impacts upon such a cuff it usually creates a hole or holes therein whereby the inflating medium escapes with a resultant deflation of the cuff and undesirable and potentially dangerous mixing of the environments normally separated by the cuff.

A method to prevent such an occurrence by disposing a thermal shield, comprising a plurality of laser-*reflecting* petals extending from the outer walls of said tubes to the inner walls of the cavity, between the cuff and the portion of the cavity wherein the surgery or treatment is to be performed, is taught in U.S. Pat. No. 4,378,796.

However, as the above shield functions by "reflecting" the laser beam its use would be diadvantageous to the patient in that the reflected beam may then impact upon healthy tissue, rather than on the surgical site, with deleterious effects thereto.

Additional protection against such undesired impact by the "laser beam [may be provided] by wrapping the tube with an aluminum adhesive tape". . . However, [a]lthough the aluminum tape provides protection, it should not be relied on heavily. . . The tape is only a safety factor and is not absolute." Ibid, p. 77.

Another problem, the destruction of viable tissue near the operative site is due to the fact that, during surgery using lasers, it is often impossible to concentrate the laser exactly and exclusively on the surgical site. For instance, the incident beam may have a larger diameter than the surgical site or part of the beam may be dispersed or reflected, although at a lower intensity, to a distance from the surgical site. This results in undesirable destruction of healthy tissue at the periphery of, and/or at a distance from, the surgical site. The damage occurs in the same manner as the surgery is effected, i.e., by ablative removal of the water (about 90%) and organic matter of which the tissue is comprised.

It has now been found that the articles of the instant invention obviate the above problems thereby providing for enhanced protection of humans, animals and articles during laser-effected surgery and treatments whereby healing of the wounds is facilitated.

SUMMARY OF THE INVENTION

Accordingly, it is an object of this invention to provide articles for the protection of humans, animals and other articles from damage due to undesireable exposure to stray or reflected laser beams used during laser-effected surgery.

It is yet another object of the invention to provide an article for the protection of humans, animal and articles from damage due to exposure to laser beams during treatment or surgery using lasers said article comprising a hydrophilic xerogel. According to another object of the invention there is provided such an article in the form of sheets, tubes, tapes and the like which are disposed between said lasers and the items to be protected.

Yet another object of the invention is to provide an article as described above further comprising a metallic backing to the xerogel adjacent the side of said xerogel distal from the incident laser beams.

Another object of the invention is to provide an article as described above wherein said xerogel further comprises pigments to additionally prevent exposure to said laser beams.

According to another object of the invention there is provided a protective article as described above wherein the proximal surface of said metallic backing is non-reflective of said laser beams thereby providing additional protection against exposure to said laser beams.

Another object of the invention is to provide a protective article as described above comprising a surgical drape for use in laser-effected treatment and surgery, comprising a sheet having a hole therethrough, for the unimpeded passage of the laser beam, to prevent said beam from impacting upon areas of the tissue other than the desired surgical or treatment site on the opposite side of the hole.

Another object is to provide a surgical drape which conforms to the tissue topography thereby precluding the existence of gaps between the tissue surface and the drape.

These and other objects of the invention will be in part discussed and in part apparent upon consideration of the detailed description of the preferred embodiment.

BRIEF DESCRIPTION OF THE DRAWINGS

FIG. 5 is a perspective view of yet another embodiment of the protective barrier according to the instant invention.

FIG. 6 is a sectional view of the embodiment of FIG. 5 along line 3—3 thereof.

DETAILED DESCRIPTION OF THE PREFERRED EMBODIMENT

Figure 1:
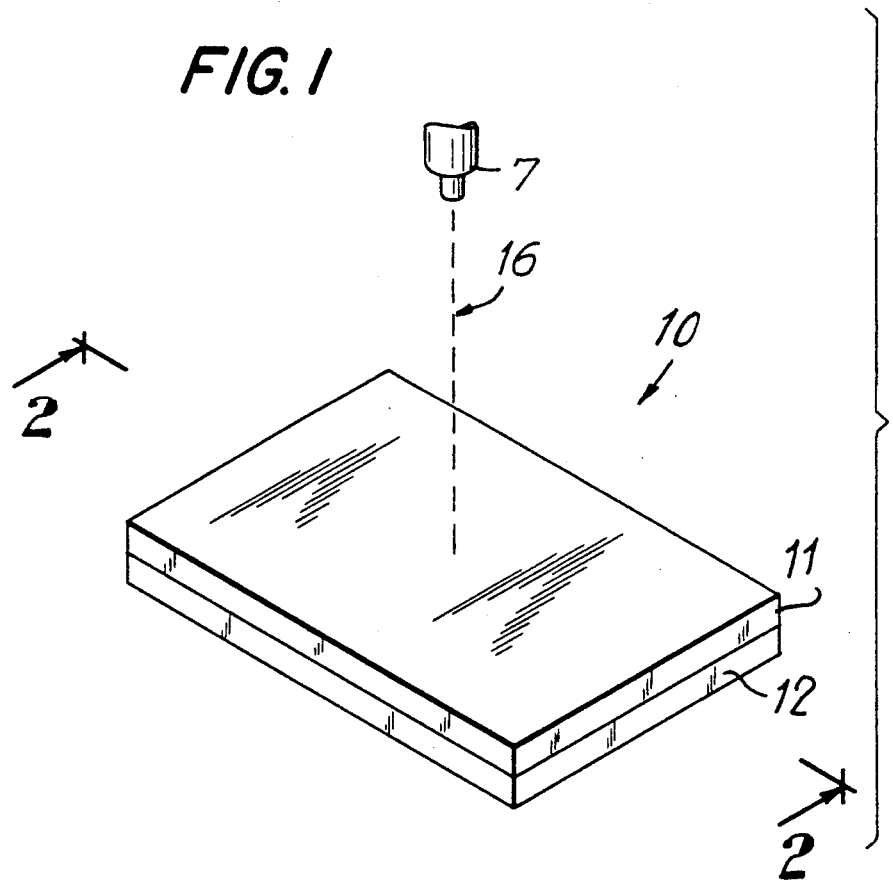
FIG. 1 is a perspective view of the protective barrier according to the instant invention.

In accordance with the invention it has now been found that humans, animals and articles may be protected from damage due to undesired exposure to laser beams by disposing protective barriers, comprising at least one xerogel, between said laser beams and the item to be protected said xerogel comprising at least one hydrophilic water-insoluble polymer.

Thus, in accordance with this invention there is provided an article for the protection of humans, animals and articles from damage due to undesired exposure to laser beams comprising A. A hydrophilic xerogel comprising at least one water-insoluble hydrophilic polymer;
B. Water; and
C. If desired, at least one additive such as a medication, colorant, pigment or moisturizer.

The hydrophilic polymers useful in accordance with the invention are those which are inherently water-insoluble and those which may be rendered so by crosslinking.

Examples of inherently water-insoluble hydrophilic polymers include copolymers of hydrophobic monomers, such as acrylonitrile, acrylates, (e.g., methyl and ethyl) methacrylates, (such as methyl and propyl) and styrene with hydrophilic monomers such as, acrylamide and acrylic and methacrylic acids. Other inherently water-insoluble hydrophilic polymers may be exemplified by hydrophobic polymers such as silicone, acrylate, methacrylate and urethane polymers whose surfaces have been rendered hydrophilic by treatments such as partial hydrolysis of e.g., ester and amide groups and by grafting of hydrophilic monomers or other functional groups to the hydrophobic backbones.

The inherently water-insoluble hydrophilic polymers useful in the practice of the instant invention include the acrylonitrile-acrylamide copolymers described in U.S. Pat. No. 4,331,783 (issued 5/25/82) and the modified acrylonitrile-acrylamide copolymers described in U.S. Pat. No. 4,337,327 (issued 6/29/92), both patents being incorporated herein for reference.

Other polymers of this nature include block copolymers of poly(ethylene oxide) and relatively hydrophobic materials such as polyurethanes which are described, e.g., by E. W. Merrill and E .W. Salzman in their article "Poly(ethylene oxide) as a Biomaterial" (Am. Soc. for Artificial Internal Organs Journal, April/June 1983, pp. 60-64). Such materials are exemplified by Polyox ™, a crosslinked poly(ethylene oxide).

Water-soluble polymers which may be rendered insoluble by crosslinking include polymers of hydrophilic monomers such as those mentioned above, hydroxyalkyl acrylates and methacrylates and alkylene oxides such as those of ethylene and propylene. Such crosslinked hydrogels are described in, e.g., U.S. Pat. No. 3,320,960 (issued 11/30/65) and U.S. Pat. No. Re 27,401 (6/20/72).

Preferred insoluble hydrophilic polymers useful in the practive of the invention are the acrylonitrile-acrylamide and poly(ethylene oxide) copolymers described above.

The particular choice of water-insoluble hydrophilic polymers for use in the articles according to the invention will depend on the specific purpose to which the article is to be applied. For instance, if the article is to be used extracorporeally, e.g., as an article of clothing, the polymer type is unlimited, whereas if the article is to be used in contact with the body, e.g., in an endotracheal tube the type of polymer will depend on, for instance, the $pK_a$ thereof and any other factors which could affect biocompatability with the specific body part in contact with the protective article.

Crosslinking may be effected by addition of crosslinking compositions, such as those which decompose into free radicals and polyfunctional materials; by exposure to radiation and by other means known to those skilled in the art.

Examples of compositions which decompose to form free radicals are azonitriles, such as azobis(isobutyronitrile); peroxides, such as benzoyl peroxide; and hydroperoxides, such as cumene hydroperoxide.

Polyfunctional materials useful in crosslinking hydrophilic polymers include the acrylates and methacrylates of polyhydric compounds such as diols, e.g., ethylene glycol; triols, such as glycerol and 1,1,1-tris(hydroxymethyl)propane; tetraols, e.g., pentaerythritol and polyhydric polymers such as epoxy resins. Other crosslinking agents which may be used in the practice of the invention, as well known in the art, include zinc oxide, organotin compounds, N,N'methylenebisacrylamide and diallylidene pentaerythritol.

Radiation-induced crosslinking may be effected by actinic radiation such as UV and visible light; $\gamma$-radiation; and electron beams.

As the sources of laser light provide light of varying wave-lengths (e.g., the $CO_2$ laser @10.6$\mu$, the Argon laser @0.48$\mu$ [i.e., in the blue region of the spectrum] and the ruby laser in the red region at 0.69$\mu$) it is often necessary to add colorants to the hydrogel to prevent transmission of the laser beams therethrough. Added colorants are not needed only in the case of the $CO_2$ laser, whose light is strongly absorbed by water and, therefore, all tissues.

If the article is to be used in contact with the body the particular crosslinking method must be such as will yield a product which will not depolymerize or decompose, to products which are water-soluble, when exposed to the body environment in which they are used or the operating media.

The protective article may be of any shape or form known in the art such as, sheets, sheaths, tape, dressings, fiber optic tubes, surgical drapes, including laser-transmitting tubes, such as vaginal dilators and retractors, and the like, and endotracheal tubes. The particular form to be used at any one time would depend upon the requirement of the user. The protective articles may be adhesive or non-adhesive and the adhesion may be autoadhesion or effected through other adhesives.

In accordance with one embodiment invention the laser barrier comprises a drape which may be placed on the item to be protected or spaced therefrom. Thus, the drape may, e.g., be placed around a surgical site, wrapped around gas cylinders within the operating room, worn as protective clothing or hung from supports within the operating room, and the like.

According to one aspect of this embodiment there is provided a surgical drape said drape comprising a sheet having a hole therethrough, said hole having about the same dimensions as the site of surgery or treatment, to permit unimpeded passage of the beam therethrough and access only to the site to be lased comprising at least one layer comprising a hydrophilic xerogel comprising at least one hydrophilic water-insoluble polymer said layer being the one proximal to the incidence of the laser beam.

It is also preferable that the drape will be made to adhere and conform to the topography of the site to preclude occlusion of gases and/or heat which might damage the tissue.

In another aspect of this embodiment said drape comprises two layers of any of the aforementioned hydrogels having a layer comprising a metallic sheet disposed therebetween and in contact with the inner surfaces thereof thereby enhancing the barrier properties thereof. I.e., the laser barrier properties of such a protective article are greater than expected from simply adding the barrier properties of the two separate hydrogel layers and the metallic sheet. If desired, only one layer of hydrophilic xerogel or hydrogel need be used. In that case the hydrogel or hydrophilic xerogel must be the layer first exposed to the laser beam.

In yet another aspect of the above embodiment the article of the invention may be utilized to protect personnel, animals and other articles in the operating room.

Thus, the protective article may be disposed as one or more hanging sheets between the personnel in the operating arena and the lasing instrument or it may be worn in the form of clothing, etc.

It may also be used by being wrapped around instruments, such as laryngoscopes, and gas cylinders as well as other ways known in the art.

In the case of, e.g., neck surgery, the protective article, in the form of sheets, may be spread on or wrapped around parts of the body adjacent to the opposite sites.

Other methods of using the protective articles will be determined by one skilled in the art in accordance with the specific application.

The metal sheets useful in accordance with this embodiment are selected from the group comprising aluminum, gold, titanium, silver, their alloys, and the like. Preferred metals for use in accordance with the invention are aluminum and gold and their alloys. The most preferred metal for use in accordance with the invention is aluminum.

It has been observed that if the lasers are used improperly during said surgery or therapy, e.g., for an excessive amount of time, the beams may burn through the hydrogel layer.

That problem may be reduced or elimated, in accordance with this invention, by modifying the above articles by dispersion of pigments in the proximal hydrogel layer.

Such problems may also be reduced or elimated by rendering the proximal surface of the metallic layer, if any, non-reflective.

If desired the hydrogel layer may comprise pigments and the proximal surface of the metallic layer rendered non-reflective.

Pigments useful in the practice of this aspect of the invention include inorganic and organic pigments preferably inorganic pigments selected from the group comprising $TiO_2$, $ZnO$, the basic white carbonates, sulfates, and silicates of lead, $ZnO$, lithopone, $Sb_2O_3$, $CaCO_3$, silicates of Mg and Al, pyrophillite, bentonite, mica, pumice, $BaSO_4$, $CaSO_4$, $MgO$, $SiO_2$, diatomite, and powders of Al, Cu, Zn, Pb, Au, Ag, Ni and their alloys, bronzes and Stainless Steel. A most preferred pigment for use in this aspect of the invention is $TiO_2$.

In accordance with another aspect of the above embodiment the barrier properties of the protective article are further enhanced by rendering the proximal surface of the metallic layer non-reflective of the laser beams.

Another embodiment of the invention provides a method of protecting humans, animals and other articles from damage caused by stray laser beams during laser-effected treatment or surgery and comprises the steps of 1. disposing an article comprising a hydrogel comprising
(a) a hydrophilic xerogel comprising at least one water-insoluble hydrophilic polymer;
(b) water; and
(c) if desired, at least one additive selected from the group comprising medications, colorants, pigments and moistureizers;
between said laser beams and the items to be protected therefrom; and 2. as necessary, water or aqueous solutions of additives may be added to the protective article to replace any water which may have been lost during the treatment or surgery.

In one aspect of this embodiment said article may be used in the form of, e.g., a sheath wrapped around a cylinder, protective clothing, sheets hanging from supports, and the like.

Specific uses to which this aspect of the embodiment may be applied will not be discussed further as they are well known to the art and will be selected according to the needs of the operator.

In another aspect of this embodiment there is provided a method of protecting healthy tissue, of an organ, from damage caused by stray laser beams during laser-effected treatment or surgery of said organ and comprises the steps of 1. applying to said organ a drape comprising a sheet having a hole therethrough, said hole having about the same dimensions as the site of tissue exposure, to permit unimpeded passage of the beam therethrough and access to only the site to be lased said sheet comprising a hydrogel comprising
(a) a hydrophilic xerogel comprising at least one water-insoluble hydrophilic polymer; and
(b) water; and
(c) if desired, at least one additive selected from the group consisting of medications, colorants, pigments and moistureizers; and 2. adding, as necessary, water or aqueous solutions of additives may be added to the protective article to replace any water which may have been lost during the treatment or surgery.

In a modification of the above aspect said drapes comprise at least one metallic layer adjacent to the side of said hydrogel distal from the incident beams.

If desired, the proximal surface of said metallic layer may be rendered non-reflective of said laser and/or said xerogel layer may further comprise a pigment dispersed therethrough. A preferred pigment for use in accordance with this aspect of the invention is $TiO_2$.

It is believed, although the theory is not essential to the practice of the invention, that the article protects the covered portions of the tissue by absorption of the energy of the laser beam incident thereon in the contained water which dissipates the absorbed energy by evaporation. A portion of the energy is also believed dissipated by scission of the organic portion of the article and ablation thereof.

Figure 2:
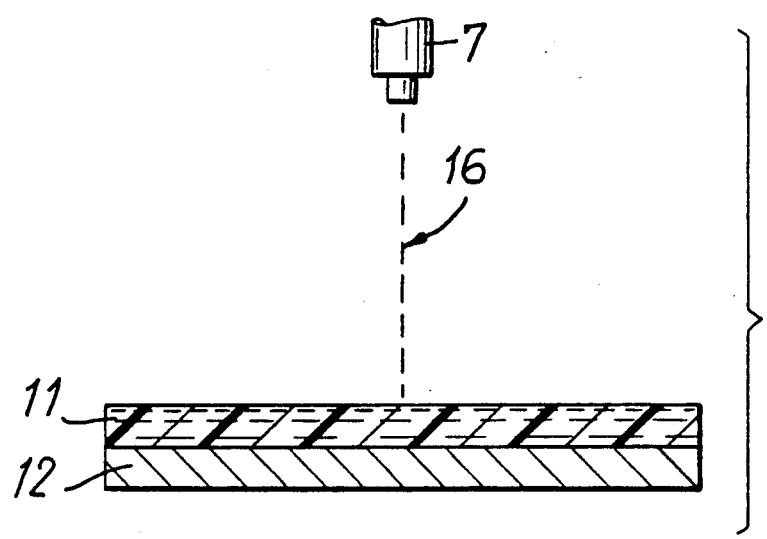
FIG. 2 is a sectional view taken along line 2—2 of FIG. 1.

In FIGS. 1 and 2 there is shown a protective article 10 according to one embodiment of the invention. (Throughout this description similar numbers will be used to indicate similar features.)

The protective article 10 comprises
(a) a first member 11 comprising a xerogel wherein the xerogel comprises at least one water-insoluble hydrophilic polymer;
(b) a second, backing, member 12; and
(c) if desired, an adhesive disposed on the side of said second members opposite the one facing the laser source 7 to provide adhesion to the body tissue upon contact therewith.

As desired water may be added to the xerogel layer just prior to placement of the article or prior to application of the laser.

Figure 3:
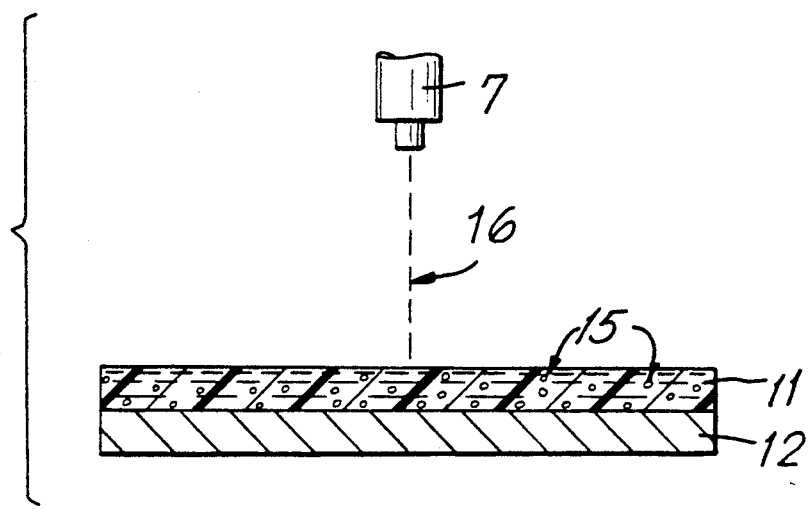
FIG. 3 is a sectional view of another embodiment of the instant invention.

In FIG. 3 there is illustrated a modification of the above embodiment wherein said xerogel layer 11 further comprises at least one pigment.

According to another aspect of embodiment there is provided a protective article (not shown) comprising three layers wherein a metallic layer is disposed between the layers 11 and 12 of FIGS. 1 and 2.

In all multilayered modifications of the invention the various layers may be made to adhere to each other either by self-adhesion or by means of adhesives disposed therebetween.

Figure 4:
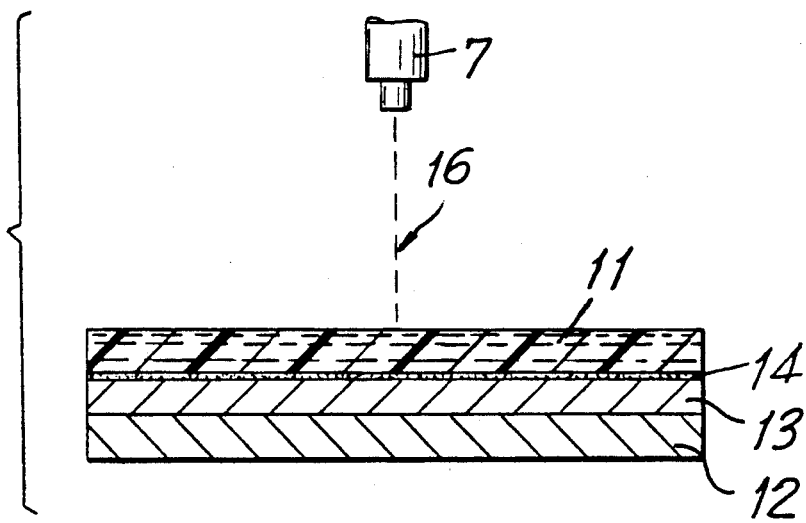
FIG. 4 is a sectional view of yet another embodiment of the instant invention.

A modification of the above aspect is illustrated in FIG. 4 wherein the proximal surface 14 of the metallic layer 13 is non-reflective of the incident laser beams 16.

If desired the modification of FIG. 4 may be further modified by dispersing pigments through the xerogel layer 11 as shown in FIG. 3.

FIGS. 5 and 6 illustrate another embodiment of the invention 20 comprising a modification of the barrier 10 wherein a hole 17 is provided through layers 11 and 12 to permit the passage of the laser beam 16 from the source 7 to the surgical site disposed below said hole.

If desired, modifications similar to those made with respect to the modifications shown in FIGS. 2 to 4 may be made in the embodiment 20.

In another modification of this embodiment as shown in FIG. 6 the drape 20 further comprises an adhesive layer 18 on the distal side of layer 12 is provided to facilitate conforming contact of the drape with the tissue.

In the practice of the invention the hydrophilic xerogels are hydrated, by either water or aqueous solutions of the aforementioned additives, prior to, or after, disposition of the articles and prior to aplication of the laser beams.

Here again, as required, water or an aqueous solution of the additives may be applied to the protective article to replace any water lost during the treatment, e.g., by ablation due to the laser energy absorbed and/or evaporation to the environment.

Methods for preparing the articles of the invention are known to the art and will not be discussed further.

Changes may be effected with respect to the details of construction and use of the invention without departing from the spirit and scope thereof as defined by the appended claims.

I claim:

1. A formed article for use in laser beam-effected surgery and therapy on humans and animals which reduces or eliminates undesired exposure of objects such as humans animals and other articles to said lasers by interposition between stray laser beams, emitted during said surgery or therapy, from which said objects are to be protected and said objects wherein said article consists of at least two layers wherein
   (a) the first layer, proximal to the stray laser beams consists of a xerogel consisting of at least one water-insoluble hydrophilic polymer; and
   (b) a second layer, on the side of the first layer distal from the stray beams consisting of a metallic layer.

2. The article according to claim 1 wherein said xerogel layer further comprises water.

3. The article according to claim 1 further comprises said xerogel layer at least one additive selected from the group consisting of pharmaceutically acceptable salts, colorants, pigments and medications.

4. The article according to claim 1 wherein the hydrophilic water-insoluble polymer is selected from the group consisting of acrylonitrile-acrylamide copolymers and crosslinked poly(ethylene oxide)s.

5. The article according to claim 4 wherein the hydrophilic water-insoluble polymer is an acrylonitrile-acrylamide copolymer.

6. The article according to claim 4 wherein the hydrophilic water-insoluble polymer is a crosslinked poly(ethylene oxide).

7. The article of claim 1 wherein said metallic layer comprises at least one metallic composition selected from the group consisting of aluminum, titanium, silver, gold and their alloys.

8. The article of claim 7 wherein said metallic composition is aluminum.

9. The article of claim 1 wherein the surface of said metallic layer, adjacent said first xerogel layer is non-reflective of said laser beams.

10. The article of claim 1 wherein said first layer further comprises pigments selected from the group consisting of inorganic and organic pigments.

11. The article of claim 10 wherein said organic pigments are selected from the group consisting of azo, nitro, anthraquinone, indigo and thioindigo pigments.

12. The article of claim 10 wherein said inorganic pigments are selected from the group consisting of $TiO_2$, ZnO, the basic white carbonates, sulfates, and silicates of lead, ZnO, lithopone, $Sb_2O_3$, $CaCO_3$, silicates of Mg and Al, pyrophillite, bentonite, mica, pumice, $BaSO_4$, $CaSO_4$, MgO, $SiO_2$, diatomite, and powders of Al, Cu, Zn, Pb, Au, Ag, Ni and their alloys, bronzes and Stainless Steel.

13. The article of claim 12 wherein said pigment is selected from the group consisting of $TiO_2$, ZnO, $Sb_2O_3$, silicates of Mg and Al, pyrophillite, bentonite, mica and pumice and powdered Al.

14. The article of claim 13 wherein said pigment is $TiO_2$.

15. The article of claim 1 wherein the form of said article is selected from the group consisting of sheaths, sheets, tapes and tubes and coatings.

16. The article of claim 15 consisting of a sheet.

17. The article of claim 15 consisting of a tubular sheath.

18. The article of claim 20 wherein said sheath comprises a sealable lengthwise opening.

19. The article of claim 15 consisting of a tape.

20. The article of claim 15 consisting of a tube.

21. The article of claim 16 wherein said article consists of a sheet having a hole therethrough, said hole having about the same dimensions as the site of desired exposure.

22. The article according to claim 21 wherein the hydrophilic water-insoluble polymer is selected from the group consisting of acrylonitrile-acrylamide copolymers and crosslinked poly(ethylene oxide)s.

23. The article of claim 21 wherein said metallic layer comprises at least one metallic composition selected from the group consisting of aluminum, titanium, silver, gold and their alloys.

24. The article of claim 23 wherein said metallic composition is aluminum.

25. The article of claim 21 wherein said xerogel layer consists of pigments comprising inorganic and organic pigments.

26. The article of claim 25 wherein said inorganic pigments are selected from the group consisting of $TiO_2$, ZnO, the basic white carbonates, sulfates, and silicates of lead, ZnO, lithopone, $Sb_2O_3$, $CaCO_3$, silicates of Mg and Al, pyrophillite, bentonite, mica, pumice, $BaSO_4$, $CaSO_4$, MgO, $SiO_2$, diatomite, and powders of Al, Cu, Zn, Pb, Au, Ag, Ni and their alloys, bronzes and Stainless Steel.

27. The article of claim 26 wherein said pigment is selected from the group consisting of $TiO_2$, ZnO, $Sb_2O_3$, silicates of Mg and Al, pyrophillite, bentonite, mica and pumice and powdered Al.

28. The article of claim 27 wherein said pigment is $TiO_2$.

29. The article of claim 23 wherein the surface of said metallic layer facing the incident laser beam is non-reflective of said laser beams.

30. A method for reducing or eliminating undesired exposure of objects to stray laser beams during laser-beam effected surgery or therapy on humans or animals which comprises the step of interposing a formed article comprising at least one layer consisting of a hydrogel between the article to be protected and the stray laser beam wherein said hydrogel layer is the layer proximal to the stray laser beams.

31. The method of claim 30 wherein said article comprises at least two layers wherein
   (a) the first layer, proximal to the stray laser beams comprises a hydrogel consisting of at least one water-insoluble hydrophilic polymer; and
   (b) a second layer on the side of the first layer distal from the stray beams consists of a metallic layer.

32. The method of claim 30 wherein said hydrogel is applied to the article to be protected in the form of a coating.

* * * * *